United States Patent
Richardson et al.

(10) Patent No.: US 9,878,087 B2
(45) Date of Patent: Jan. 30, 2018

(54) PUMP-INFLOW-CANNULA, A PUMP-OUTFLOW-CANNULA AND A BLOOD MANAGING SYSTEM

(75) Inventors: J. Scott Richardson, Wilmington, MA (US); Barry N. Gellman, North Easton, MA (US); Andrew Koert, Somerville, MA (US); Kurt Dasse, Wellesley, MA (US)

(73) Assignee: TC1 LLC, St. Paul, MN (US)

( * ) Notice: Subject to any disclaimer, the term of this patent is extended or adjusted under 35 U.S.C. 154(b) by 0 days.

(21) Appl. No.: 13/349,462

(22) Filed: Jan. 12, 2012

(65) Prior Publication Data

US 2012/0220815 A1    Aug. 30, 2012

Related U.S. Application Data

(62) Division of application No. 11/698,322, filed on Jan. 26, 2007, now Pat. No. 8,118,723.

(Continued)

(51) Int. Cl.

| | |
|---|---|
| *A61M 1/12* | (2006.01) |
| *A61M 25/00* | (2006.01) |
| *A61M 1/36* | (2006.01) |
| *A61M 1/10* | (2006.01) |
| *B33Y 80/00* | (2015.01) |
| *B33Y 70/00* | (2015.01) |

(52) U.S. Cl.
CPC ........ *A61M 1/3653* (2013.01); *A61M 1/1008* (2014.02); *A61M 1/122* (2014.02);
(Continued)

(58) Field of Classification Search
CPC ........ A61M 1/12; A61M 1/122; A61M 1/125; A61M 1/3653; A61M 1/3659; A61M 1/3666; A61M 1/1008
(Continued)

(56) References Cited

U.S. PATENT DOCUMENTS

| | | |
|---|---|---|
| 4,455,690 A | 6/1984 | Homsy |
| 5,061,256 A | 10/1991 | Wampler |

(Continued)

FOREIGN PATENT DOCUMENTS

| | | |
|---|---|---|
| DE | 101 08 809 A1 | 9/2002 |
| EP | 1 462 133 A2 | 9/2004 |

(Continued)

*Primary Examiner* — Catherine Voorhees
*Assistant Examiner* — Pamela M Bays
(74) *Attorney, Agent, or Firm* — Kilpatrick, Townsend & Stockton LLP

(57) ABSTRACT

The invention relates to a pump-inflow-cannula (1) providing a blood conduit from a heart (2) and/or from an associated vessel to an external blood handling system. The pump-inflow-cannula comprises a body (3), encompassing an essentially axially extending inflow-lumen (4), having a distal-end (5) for an attachment of the inflow-lumen (4) to the blood handling system, and having a proximal-end (6) for an introduction of blood from the heart (2) and/or from the associated vessel into the inflow-lumen (4), wherein at least one projection (7) is provided at the proximal-end (6) to deflect a heart muscle from intruding into the inflow-lumen (4), wherein the body (3) of the pump-inflow-cannula comprises a reinforcement-means (8). The invention is also related to a pump-outflow-cannula (19) and to a blood managing system comprising a pump-inflow-cannula and a pump-outflow-cannula in accordance with the present invention.

20 Claims, 10 Drawing Sheets

Related U.S. Application Data

(60) Provisional application No. 60/776,358, filed on Feb. 23, 2006.

(52) U.S. Cl.
CPC ........ *A61M 1/3659* (2014.02); *A61M 1/3666* (2013.01); *A61M 1/10* (2013.01); *A61M 1/1006* (2014.02); *A61M 1/12* (2013.01); *B33Y 70/00* (2014.12); *B33Y 80/00* (2014.12)

(58) Field of Classification Search
USPC ............... 600/16, 17; 604/264, 523, 533
See application file for complete search history.

(56) References Cited

U.S. PATENT DOCUMENTS

| | | | | |
|---|---|---|---|---|
| 5,931,801 | A * | 8/1999 | Burbank | A61M 1/3653 604/4.01 |
| 6,050,975 | A * | 4/2000 | Poirier | 604/131 |
| 6,102,845 | A * | 8/2000 | Woodard et al. | 600/16 |
| 2002/0082467 | A1 * | 6/2002 | Campbell | 600/16 |
| 2002/0095210 | A1 * | 7/2002 | Finnegan et al. | 623/3.26 |
| 2002/0161321 | A1 | 10/2002 | Sweezer, Jr. et al. | |
| 2003/0130668 | A1 * | 7/2003 | Nieman | A61M 1/10 606/108 |
| 2004/0034369 | A1 * | 2/2004 | Sauer et al. | 606/139 |
| 2004/0064193 | A1 | 4/2004 | Evans et al. | |
| 2004/0106931 | A1 * | 6/2004 | Guiles et al. | 606/108 |
| 2004/0122283 | A1 | 6/2004 | Nose et al. | |
| 2005/0059925 | A1 | 3/2005 | Maginot et al. | |
| 2005/0256540 | A1 * | 11/2005 | Silver et al. | 607/3 |
| 2007/0049787 | A1 | 3/2007 | Nose et al. | |

FOREIGN PATENT DOCUMENTS

| | | |
|---|---|---|
| EP | 1 462 133 A3 | 9/2004 |
| WO | WO 01/83021 A1 | 11/2001 |

* cited by examiner

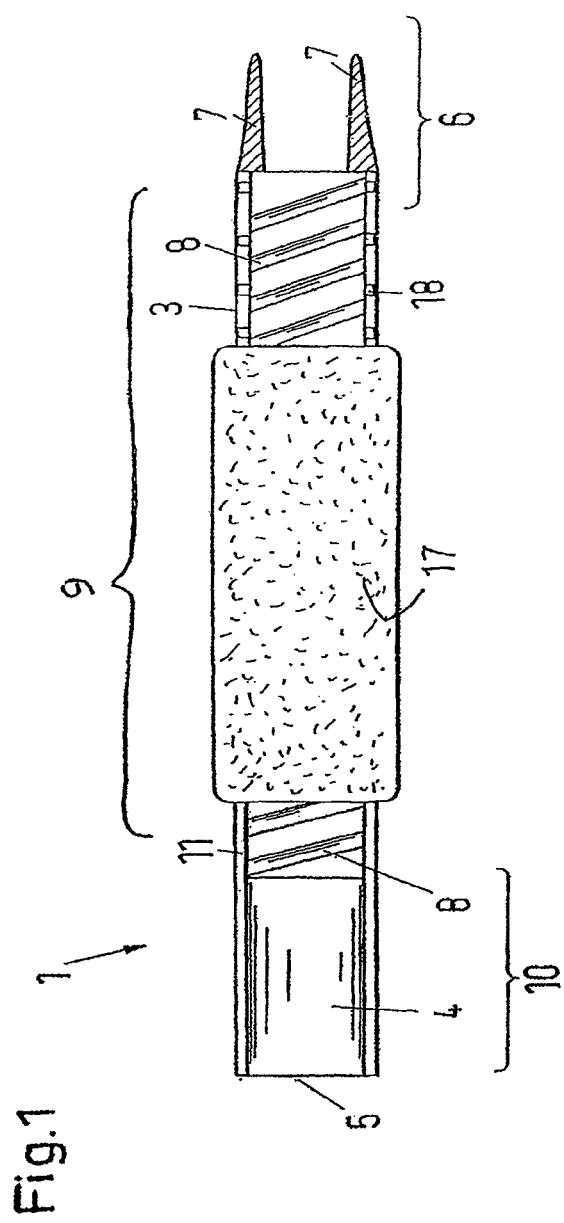

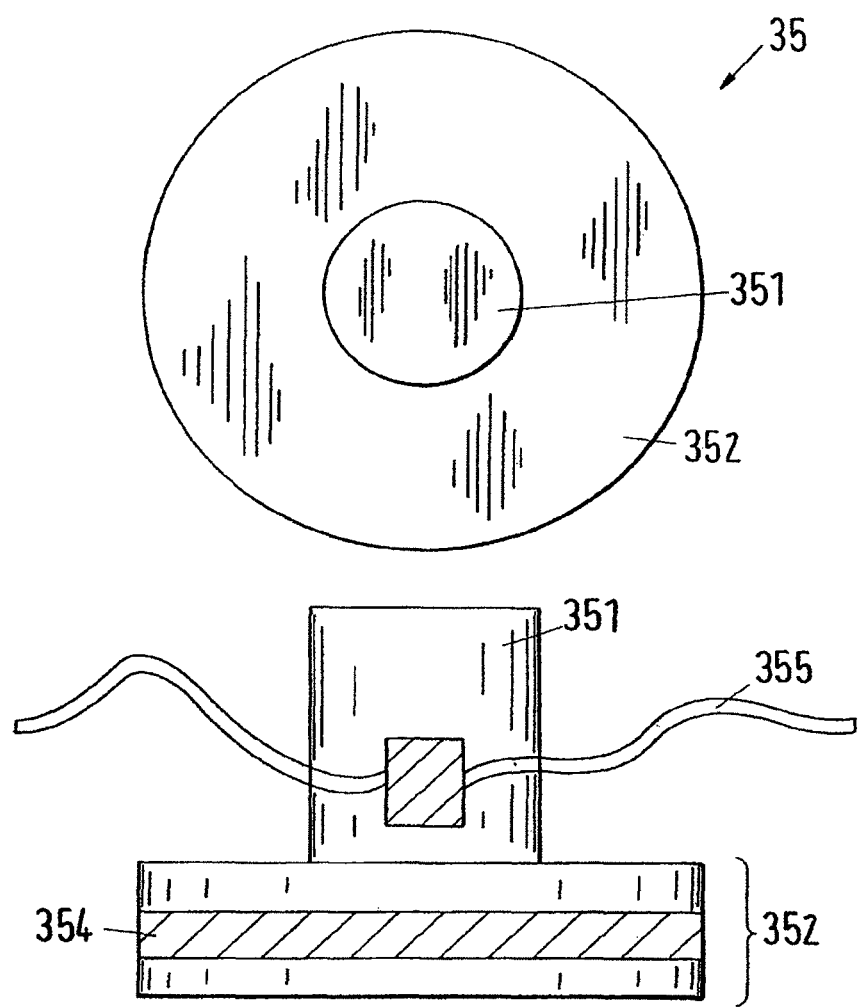

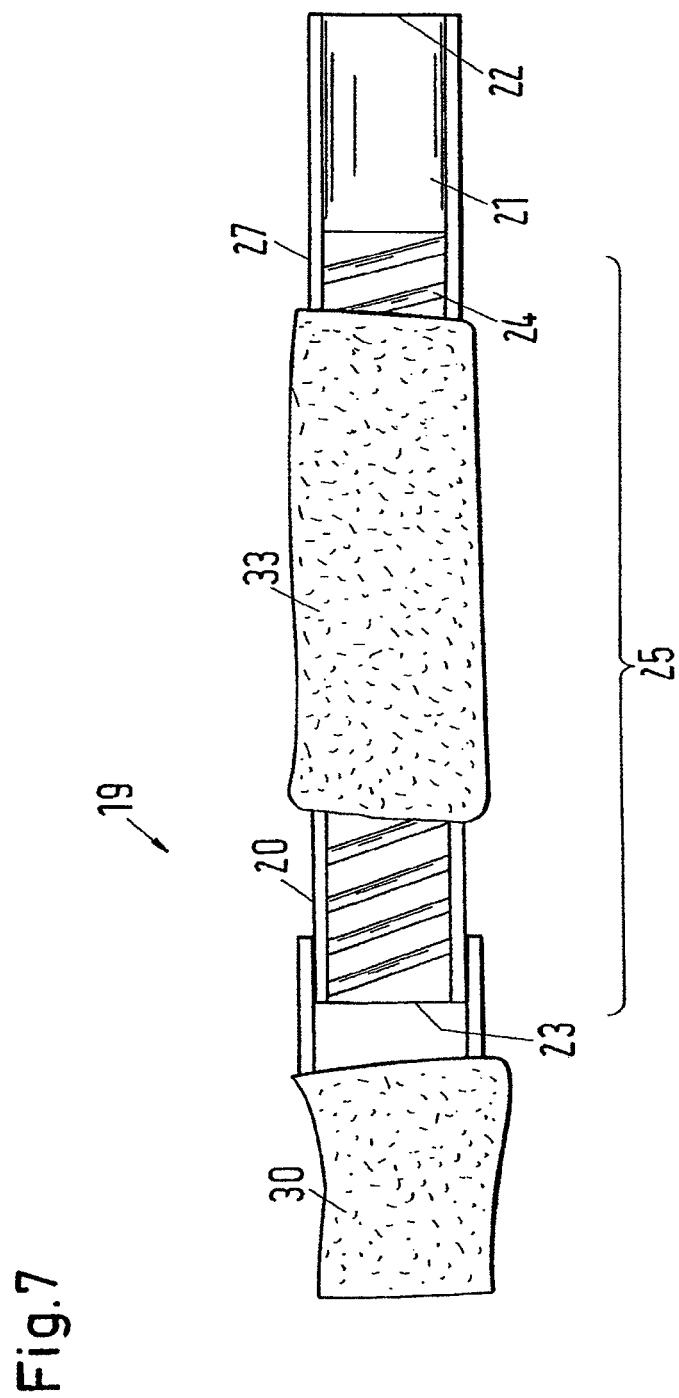

PUMP-INFLOW-CANNULA, A PUMP-OUTFLOW-CANNULA AND A BLOOD MANAGING SYSTEM

CROSS-REFERENCES TO RELATED APPLICATIONS

This is a divisional of U.S. patent application Ser. No. 11/698,322, filed Jan. 26, 2007, which claims priority to Provisional Application No. 60/776,358, filed Feb. 23, 2006. The disclosures of both of the above-referenced applications are hereby incorporated herein by reference.

STATEMENT AS TO RIGHTS TO INVENTIONS MADE UNDER FEDERALLY SPONSORED RESEARCH OR DEVELOPMENT

This invention was made with Government support under contract number 1R44HL074628-01 awarded by the National Institute of Health (NIH). The Government has certain rights to this invention.

BACKGROUND OF THE INVENTION

The invention relates to a pump-inflow-cannula and a pump-outflow-cannula providing a blood conduit from a heart and/or from an associated vessel, as well as to a blood managing system comprising a pump-inflow-cannula and/or a pump-outflow-cannula, a method for connecting a pump-inflow-cannula, a method for connecting a pump-outflow-cannula, a method for connecting a blood managing system and a method for performing a bypass.

Cardiac support systems, in particular long-term cardiac support systems, are utilized as a "bridge to decision" and a "bridge to transplant" for patients requiring physiologic cardiac stability. Such cardiac support systems are typically accomplished with an extracorporeal circuit containing a blood pump and sometimes an oxygenator which are attached to the blood circulation of a patient by a pump-inflow-cannula providing a blood conduit from the heart or from an associated vessel, e.g. from a vein to the blood pump, and a pump-outflow-cannula providing a blood conduit from the blood pump back to the heart or an associated vessel, e.g. to an arteria, in particular to the aorta. That is, the cardiac connection between the patient and the extracorporeal circuit is accomplished with the pump-inflow- and pump-outflow-cannulae that are placed within the cardiac chambers or major supply vessels.

Open heart surgery cannulae typically result in utilization of less than six hours, while "bridge" cannulae or "long-term" cannulae may be used up to six months. Cannulae utilized for extended periods of time must impose minimal trauma on the blood.

For long-term cardiac support up to six months or longer, the "UltraMag Blood Pump" from Levitronix LLC has turned out to work extremely reliably and to produce minimal blood trauma. The same is true for Levitronix's "CentriMag Blood Pump", which is intended for short-term support, typically for less than 30-day use.

The most common techniques used in Cardiac Surgery Centers for postcardiotomy support include Extracorporeal Membrane Oxygenation (ECMO) and Ventricular Assist Devices (VAD). Poor ventricular function may be diagnosed preoperatively or may have resulted from myocardial insult during surgery, for example from inadequate perfusion, cross-clamping for extended periods of time limiting reperfusion, injury, etc.

A reduced cardiac output over the years will affect other organs due to low blood pressure and blood flow. Over time, allowing the myocardium to rest may allow recovery. Thus, the patient may require long-term cardiac support. Patients who cannot be weaned from cardiopulmonary bypass and possess isolated ventricular dysfunction are probably candidates for a Ventricular Assist Device (VAD). Also well known are BiVAD support systems requiring two-pump circuits. When pulmonary dysfunction occurs, the patient is most likely a candidate for Extracorporeal Membrane Oxygenation (ECMO).

Cardiac cannulae provide the patient interface means to an extracorporeal blood circuit. A placement of these cannulae may access the vasculature through major vessels, e.g. through Right Atrium (RA), Left Atrium (LA), Left Ventricular Apex (LVA), Femoral Artery (FA), Femoral Vein (FV), Superior Vena Cava (SVC), Inferior Vena Cava (IVC) or the Aorta. Two cannulae are required in the extracorporeal circuit: one for pump inflow, the pump-inflow-cannula, and one for pump outflow, the pump-outflow-cannula.

The pump-inflow-cannula, sometimes referred to as the "venous cannula", is the primary conduit that transitions the blood from the patient to the extracorporeal circuit. The exact placement location is at the discretion of the surgeon. Ideally, the pump-inflow-cannula may be positioned within the ventricle transitioning the heart wall with the lumen of the cannula extending just past the wall. The cannula should be stabilized by a suture purse-string or a sewing-ring to provide a means for securing the cannula against inadvertent dislodgement and to provide a leak-free connection.

The pump-outflow-cannula, sometimes referred to as the "return cannula", or the "arterial cannula" (which may be a misnomer), is the primary conduit that transitions the blood from the extracorporeal circuit to the patient. The aorta is the preferred site for the pump-outflow-cannula but other sites may be selected at the discretion of the physician. The pump-outflow-cannula may be secured through the aortic arch and may be accomplished in a variety of ways. One way is to secure a vascular graft to the transverse arch and pass the pump-outflow-cannula through the graft lumen, but preferably not enter into the vessel, and to secure the graft to the cannula by wrapping a suture about the graft. Another possibility may be to place the tip of the cannula through the wall of the aorta and stabilize it with a purse-string suture or a tip-stabilizing device. The pulmonary artery is also a common point of blood return.

The distal-end of the pump-inflow-cannula, that is, the end which is connected to the extracorporeal circuit, is passed through a dilated tunnel created from the ventricle through the subcutaneous plane to the percutaneous access site. The pump-outflow-cannula is passed through a dilated tunnel created from the arch of the ascending aorta through the subcutaneous plane to the percutaneous exit site. The percutaneous access sites are located ipsilaterally, on the left abdominal wall for the Left Ventricular Assist Device (LVAD), in the medial anterior position. The location is ipsilateral on the right abdominal wall for a Right Ventricular Assist Device (RVAD), in the medial anterior position. The extracorporeal system is attached to the pump-inflow- and the pump-outflow-cannulae using good perfusion technique. The open chest wound is closed upon successfully administrating the support system.

The support system, in particular the pump-inflow- and pump-outflow-cannulae known from the state of the art, has several disadvantages, in particular with respect to the blood transfer from the heart and/or from the associated vessels into the pump-inflow-cannula as well as with respect to the transfer of the blood out of the pump-outflow-cannula into the heart or into the associated vessel. Over extended periods of time, very low flow rates can initiate blood clots that can release and become lodged down-stream in the pump, oxygenator or patient organs. Furthermore, the attachment of the known cannulae to the patient is difficult to handle and, what is more, the known cannulae can be easily compressed and/or bent, which can easily lead to a cross-clamping of the cannula, resulting in an interruption of the blood flow through the extracorporeal support system, which may cause serious consequences for the patient's physical health and, at worst, may lead to a life-threatening situation for the patient.

SUMMARY OF THE INVENTION

It is therefore an object of the present invention to provide both an improved pump-inflow-cannula and a pump-outflow-cannula as well as a blood managing system comprising such improved cannulae for establishing a blood conduit from a heart and/or an associated vessel to a external blood handling system. It is further an object of the invention to provide a method for connecting a cannula and a blood managing system in accordance with the invention to a heart and/or to an associated vessel of a human or an animal blood circulation and to propose a method for performing a bypass of a human or an animal organ.

The invention relates to a pump-inflow-cannula providing a blood conduit from a heart and/or from an associated vessel to an external blood handling system. The pump-inflow-cannula comprises a body, encompassing an essentially axially extending inflow-lumen, having a distal-end for an attachment of the inflow-lumen to the blood handling system, and having a proximal-end for an introduction of blood from the heart and/or from the associated vessel into the inflow-lumen, wherein at least one projection is provided at the proximal-end to deflect a heart muscle from intruding into the inflow-lumen, and wherein the body of the pump-inflow-cannula comprises a reinforcement-means.

A special embodiment of a pump-inflow-cannula in accordance with the present invention comprises a reinforced body-portion to be essentially contained within a corpus, especially to be contained within the corpus and extending beyond a skin of the corpus, and a compressible and/or bendable system-portion to be located outside of the corpus. The cannula portion contained within the body of the patient and slightly emerging is preferably wire reinforced to prevent collapse from tissue compression and from bending and must resist occlusion from low pressure created by the blood pump. The reinforcement-means of the pump-inflow-cannula emerging through the skin should stop outside the emergence from the corpus of the patient to enable cross-clamping the cannula without cannula damage.

To maintain a small profile, the reinforcement-means are preferably located within a wall structure of the body of the pump-inflow-cannula. In a special embodiment, the reinforcement-means is a wire, in particular a wire made of plastic and/or made of a composite material and/or made of a metal, especially made of a stainless steel, and/or the reinforcement-means is a spring, in particular a helical spring, especially a flat spring, and in more particular a flat spring being between 0.01" and 0.03" wide and being between 0.003" and 0.007" thick, in particular being 0.02" wide×0.005" thick, preferably with a pitch ranging from 0.002" to 0.040", and/or the reinforcement-means is encapsulated in a polymer. Alternatively, round wire may be used but would result in a thicker cannula wall.

Thus, the inflow-cannula in accordance with the present invention provides both a blood supply to the extracorporeal blood handling system, e.g. to a blood pump, and structural support to the conduit.

To reduce blood trauma, a blood exposed surface of the projection provided at the proximal-end is rounded.

The projection is preferably spring-reinforced by means of a tip-spring to resist flapping during blood passage and/or to provide additional resistance from inward deflection of the heart muscle from intruding into the inflow-lumen and wherein an axial extension of the projection is between 0.25" and 0.75" (between 0.64 cm and 1.91 cm), preferably 0.46" (1.17 cm), and the tip-spring has an axial extension between 0.15" and 0.70" (between 0.38 cm and 1.78 cm), preferably 0.40" (1.02 cm), and/or wherein the tip-spring is encased in the projection to avoid a contact of the tip-spring with blood.

In a special embodiment, which is very important in practice, at least two projections are provided at the proximal-end being separated by a tip-valley. The valley between the at least two projections provides a means for blood flow into the pump-inflow-cannula in case a projection is deflected inward during a contact with the heart wall. One or two lumen occlusion does not inhibit fully developed flow within the cannula. The placement of holes is common-place for this function.

The distal-end of the inflow-lumen of a pump-inflow-cannula in accordance with the present invention is a straight lumen, in particular a straight 7.2 mm lumen, and/or a convertible distal-end is provided comprising at the segment of the 7.2 mm lumen a transition to a lumen, in particular to a ⅜" (0.95 cm) lumen capable of receiving a ⅜" tube connector, in particular a barbed ⅜" tube connector.

In this convertible design, the barbed fitting and an associated tunneler cap can be utilized for initial cannula tunneling placement. The ⅜" barbed connector would be compatible with the ⅜" tubing set and can be connected e.g. to the above-mentioned Levitronix CentriMag Blood Pump or other ⅜" device. Upon patient assessment with a short-term blood pump, the cannula would be trimmed to the 7.2 mm lumen, e.g. for connection to the UltraMag Blood Pump, eliminating the need to trade-out cannulae, saving a surgical intervention.

In applications where the UltraMag Blood Pump is the primary pump interface, the cannula may be pre-selected to include the barbed tunneler-plug fitted into the 7.2 mm lumen. The plug is then trimmed or removed for direct pump attachment.

Preferably, a surface of the pump-inflow-cannula is biocompatible to blood and/or a tissue and/or the pump-inflow-cannula is made of a polycarbonate-based urethane, especially made of carbothane and/or another urethane and/or PVC, and/or vinyl materials, and/or elastomeric materials, and the cannula material durometer ranges from 50 Shore A to 100 Shore A, preferably from 70 Shore A to 90 Shore A, and/or the pump-inflow-cannula is fabricated by dip-molding, extrusion, injection molding or combinations thereof and/or is fabricated in a single polymer layer and/or in multiple polymer layers and/or in sections hermetically bonded.

In a special embodiment, to supplement the cannula sealing a wrap is provided on the surface of the body of the inflow-cannula, especially a wrap of a polyester velour material, providing a means to enable tissue in-growth. This velour provides a means to enable tissue in-growth to enter the interstitial spaces of the fabric and result in an effective seal. This tissue in-growth also provides an additional structure support to resist cannula movement and cannula pull-out.

Regarding a preferred embodiment, for indicating a placement depth from the epicardial surface of the heart, a depth-indicator may be provided and/or a radiopaque feature is provided comprising a reference feature to enable imaging of the proximal-end of the pump-inflow-cannula for post-surgical placement assessment, and the radiopaque feature is a stainless steel marking-spring incorporated in the proximal-end of the pump-inflow-cannula and/or the radiopaque feature is a marker made of tantalum and/or stainless steel and/or another radiopaque material.

In a further embodiment, the inflow-lumen of a pump-inflow-cannula in accordance with the present invention is a multi-inflow-lumen comprising at least two sub-lumens providing a passage-means for a passage of a secondary device, in particular for a passage of a diagnostic and/or a therapeutic tool, in more particular for a temperature sensing tool and/or a blood gas sensing tool and/or a pressure measuring tool and/or for a passage of a guidewire and/or a catheter and/or a passage for flushing and/or a passage for a vascular injection and/or another passage-means.

The present invention is also related to a pump-outflow-cannula providing a blood conduit from an external blood handling system to a heart and/or to an associated vessel. The pump-outflow-cannula comprises a body encompassing an essentially axially extending outflow-lumen having a distal-end for an introduction of blood from the blood management system into the outflow-lumen, and having a proximal-end for an attachment of the outflow-lumen to the heart and/or to the associated vessel, wherein the body of the pump-outflow-cannula comprises a reinforcement-means.

Regarding a preferred embodiment of a pump-outflow-cannula in accordance with the present invention, the pump-outflow-cannula comprises a reinforced body-portion to be essentially contained within a corpus of a human or an animal, especially to be contained within the corpus and extending beyond a skin of the corpus, and comprising a compressible and/or bendable system-portion to be located outside of the corpus.

The reinforcement-means are preferably located within a wall structure of the body of the pump-outflow-cannula, and/or the reinforcement-means may be a wire, in particular a wire made of plastic, and/or made of a composite material, and/or made of a metal, especially made of a stainless steel. The reinforcement-means can be a spring, in particular a helical spring, especially a flat spring, and in more particular a flat spring being between 0.01" and 0.03" wide and being between 0.003" and 0.007" thick, in particular being 0.02" wide×0.005" thick, preferably with a pitch ranging from 0.002" to 0.040", and/or the reinforcement-means is encapsulated in a polymer.

Thus, the pump-outflow-cannula in accordance with the present invention provides both a blood supply from the extracorporeal blood handling system, e.g. from a blood pump, and structural support to the conduit.

In a special embodiment, at the distal-end of the outflow-lumen a straight lumen, in particular a straight 7.2 mm lumen, is provided and/or a convertible distal-end is provided comprising at the segment a transition to a lumen, in particular to a ⅜" lumen capable of receiving a ⅜" tube connector, in particular a barbed ⅜" tube connector.

In a preferred embodiment of a pump-outflow-cannula in accordance with the present invention, the proximal-end comprises a securing-means for securing the proximal-end to the heart and/or to the associated vessel, in particular a vascular graft and/or an embedded winding for securing a vascular graft.

The proximal-end of a pump-outflow-cannula preferably comprises a fluid-deflection for controlling the blood flow into a vessel, in particular a fluid-deflection with hardened deflection-tip, wherein the deflection-tip is straight or bent 1° to 60°, preferably 5° to 30° from a longitudinal axis of the outflow-lumen.

Regarding a special embodiment which is very important in practice, a surface of the pump-outflow-cannula is biocompatible to blood and/or a tissue, and/or the pump-outflow cannula is made of a polycarbonate-based urethane, especially made of carbothane and/or another urethane and/or PVC, and/or vinyl materials, and/or elastomeric materials, and the cannula material durometer ranges from 50 Shore A to 100 Shore A, preferably from 70 Shore A to 90 Shore A, and/or the pump-inflow-cannula is fabricated by dip-molding, extrusion, injection molding or combinations thereof and/or is fabricated in a single polymer layer and/or in multiple polymer layers and/or in sections hermetically bonded.

Preferably, a wrap is provided on the surface of the body of the inflow-cannula, especially a wrap of a polyester velour material, providing a means to enable tissue in-growth, and/or a depth-indicator is provided for indicating a placement depth into the vessel.

The invention is furthermore concerned with a blood managing system comprising a pump-inflow-cannula and/or a pump-outflow-cannula in accordance with the present invention.

A blood managing system in accordance with the invention comprises preferably a tunneler-plug to assist the pump-inflow-cannula and/or the pump-outflow-cannula in tunneling through a tissue of a corpus. To assist in tunneling the cannula through the tissue, the tunneler-plug is attached to the distal-end into the exit lumen of the respective cannula. The tunneler-plug includes a barbed fitting on one end and a smooth tapering section on the other end to ease passage as it (with its assembled cannula) dilates a lumen during passage. The tunneler-plug is made of rigid polymer or metal (polycarbonate is preferred) and may be produced by injection molding, machining, casting or stereolithography (rapid prototyping) for short-term body contact. The distal tunneler-plug may also include a means to secure a suture or umbilical tape to create a tether for assisting in pulling the assembly through the tissue.

Upon completion of passage of the cannula outside the body, the tunneler-plug may be disconnected or cut-off from the cannula and the distal portion of the cannula is attached to the extracorporeal blood handling system.

Prior to insertion of the cannula into the ventricle of the heart, to securely locate the pump-inflow-cannula into a heart, a sewing-ring is provided.

The sewing-ring is positioned at the apex of the heart and sewn in place to the exterior heart muscle. Once secured, an incision made with a scalpel or coring knife is advanced through the heart wall to enable cannula passage.

Alternatively, a cannula-tip-stabilizer is provided to secure the pump-inflow-cannula and/or the pump-outflow-cannula to the heart and/or to an associated vessel, especially using purse-string sutures. The tip-stabilizer provides a wrapping means for the suture and protects the cannula from being cut into by the suture when tightened. In addition, the cannula-tip-stabilizer enables the sutures to be positioned as close to the entry site as possible with a little compression beneath the stabilizer to affect positioning or compression/abrasion.

The cannula may contain a number of securing grommets slideable along the cannula length for the surgeon to suture strain-relief at strategic locations along the implant.

In a further embodiment, a stabilizing-ring is provided to secure the pump-inflow-cannula and/or the pump-outflow-cannula with a suture. The stabilizing-ring should enable the cannula to be secured with sutures without resulting in the occlusion of the cannula lumen. The securing grommets are designed to fit about the outside diameter of the cannula. Its shape should provide a means for wrapping a suture while providing a feature to keep the suture from inadvertently sliding off. The grommet may be made from silicone, polyurethane, TPR rubber, or other elastomeric material compatible for long-term implant. The grommet may be injection molded, cast, or formed. The stabilizer-ring may also be filled with a radiopaque material so that it is visible via x-ray or fluoroscopic inspection. The number of grommets utilized are at the discretion of the physician to hold the internal cannula shape.

For the placement of the pump-inflow-cannula and/or the pump-outflow-cannula into the vessel an introducer is provided, to enable easy placement into the vessels utilizing a guidewire. The central lumen of the introducer is slideably fit over an 0.038" (0.965 mm) guide wire should the field be too bloody to visually see exact cannula placement. The introducer provides a resistance to blood backflow up the cannula. The slow removal of the introducer provides a controlled reversed priming of the cannula prior to assembly to the circuit. The introducer is placed after the tunneler-plug is removed and seated within the open distal-end of the cannula with the proximal-end of the introducer extending beyond the cannulae distal tip.

The diameter of the introducer is such as to permit an easy slide within the cannula inside diameter with minimal clearance to result in a smooth transition from the introducer shaft to the distal cannula. This transition should enable smooth advancing of the cannula into the vessel.

The blood managing system in accordance with the present invention may include a blood handling system, in particular a blood pump, in more particular a Levitronix UltraMag Blood Pump and/or an Levitronix CentriMag Blood Pump, or an oxygenator, especially an extracorporeal membrane oxygenator, or a dialysis apparatus, or another medical apparatus is provided for connection with the pump-inflow-cannula and/or with the pump-outflow-cannula, in particular to connect the pump-inflow-cannula with the pump-outflow-cannula.

In addition a method for connecting a pump-inflow-cannula to a heart and/or to an associated vessel of a human and/or an animal blood circulation is provided by the invention, which method comprises the following steps:

providing a pump-inflow-cannula for establishing a blood conduit from the heart and/or from an associated vessel to an external blood handling system, wherein the pump-inflow-cannula includes a body, encompassing an essentially axially extending inflow-lumen, having a distal-end for an attachment of the inflow-lumen to the blood management system, and having a proximal-end for an introduction of blood from the heart and/or from the associated vessel into the inflow-lumen. At least one projection is provided at the proximal-end to deflect a heart muscle from intruding into the inflow-lumen, wherein the body of the pump-inflow-cannula comprises a reinforcement-means;

fixing the proximal-end of the pump-inflow-cannula at the heart and/or at the associated vessel, in particular fixing the pump-inflow-cannula by a sewing technique.

The pump-inflow-cannula body is intended to provide a conduit from the blood supply to the extracorporeal device circuit located outside the body. This cannula body provides blood passage as well structural support to the conduit. In addition, the cannula body contacts both internal organs/tissues and allows external handling of the device. The cannula is "tunneled" through a passage emerging out through the skin. The reinforcement should stop outside the emergence from the body to enable cross-clamping the cannula without cannula damage. Identifiable markings on the cannula direct the user to the appropriate location to cross-clamp.

The cannula portion at the emergence site must affect tissue healing so as not to result in channeling about the cannula for bacteria to enter. To supplement the cannula sealing, a wrap of a polyester velour material is wound and attached (without channeling between the fabric and the cannula) about the cannula. This velour provides a means to enable tissue in-growth to enter the interstitial spaces of the fabric and result in an effective seal. This tissue in-growth also provides an additional structural support to resist cannula movement, skin separation during movement and cannula pull-out.

The invention relates additionally to a method for connecting a pump-outflow-cannula to a heart and/or to an associated vessel of a human and/or an animal blood circulation comprising the following steps:

providing a pump-outflow-cannula for establishing a blood conduit from an external blood handling system to the heart and/or to an associated vessel, the pump-outflow-cannula comprising a body encompassing an essentially axially extending outflow-lumen having a distal-end for an introduction of blood from the blood management system into the outflow-lumen, and having a proximal-end for an attachment of the outflow-lumen to the heart and/or to the associated vessel, wherein the body of the pump-outflow-cannula comprises a reinforcement-means;

fixing the proximal-end of the pump-outflow-cannula at the heart and/or at the associated vessel, in particular fixing the pump-outflow-cannula by a sewing technique.

The pump-outflow-cannula may be placed in a variety of ways, each with unique design configurations. In the following, three methods for placing a pump-outflow-cannula are exemplarily described.

A. The proximal-end can be positioned through the lumen within a vascular graft sutured to the major vessels (via an end-to-side anastomosis).

B. The proximal-end is positioned directly to the major vessel (via an end-to-side anastomosis).

C. The proximal tip is positioned within the major vessel and secured with a purse-string suture.

Design A incorporates a standard vascular graft (i.e. diameter 8 mm) and suturing technique to the vessel wall so as to create a side opening in the vessel for blood passage. The proximal-end of the pump-outflow-cannula is configured so as to enable positioning the cannula proximal-end into the body of the graft through the lumen. A suture is then wrapped about the graft to secure the cannula within it and provide a leak-tight joint.

The proximal-end of the pump-outflow-cannula may be placed within the lumen of a vascular graft (8 mm graft) attached to the aortic artery. The graft is intended to prevent accidental decannulation and to reduce pressure necrosis of the vessel wall by providing a "soft" interface, and a smooth cannula-to-vessel transition. Placement of the cannula within the graft and not extending the cannula into the aorta reduces dislodgement of embolic material from the return blood flow stream.

The proximal lumen of the pump-outflow-cannula is a through lumen. The periphery about the tip should be 0.315" (0.800 cm) ranging from 0.100" (0.254 cm) to 0.600" (1.524 cm).

The proximal-end of the pump-outflow-cannula is configured as a squared-off open lumen from the cannula body. The proximal tip is tapered on the inside diameter and straight walled on the outside diameter to minimize "dead space" about the cannula positioned within the lumen of the graft.

The proximal outflow-cannula diameter is sized to enable maximum blood flow and fit within the vascular graft. To accomplish this, the cannula is reinforced with flat wire, thereby having a minimal wall thickness. In such a design, the reinforcing wire provides resistance from occlusion when the suture is wrapped about the graft for securing the graft to the cannula.

Design B incorporates a standard vascular graft (i.e. diameter 8 mm) pre-attached to the pump-outflow-cannula. This graft is sutured utilizing standard end-to-side anastomosis technique to the vessel wall so as to create a side opening in the vessel for blood passage.

The proximal-end of the pump-outflow-cannula is configured to enable vascular graft attachment. A spiral wound vascular graft was selected (but not necessary) with the intent to screw-thread the graft on top of the cannula proximal-end.

A round extrusion is produced from carbothane (or the same material as the cannula), wound into a thread pitch and assembled to the distal-end of the cannula. This winding is embedded in the cannula wall so as to produce a thread on the exterior of the cannula. The vascular graft is threaded over this embedded winding for attachment. A short shrink tube or elastic sleeve (slightly smaller than the cannula outside diameter) is fitted over the assembly to mechanically lock the graft into place onto the cannula. This sleeve may be bonded to the cannula body as well.

Design C incorporates no vascular graft but rather positions the cannula proximal tip directly through the vessel wall. This cannula is purse-string secured to the vessel wall.

The proximal-end of this cannula may be straight or bent 5° to 30° from the axis to create a fluid-deflection at the outlet. Such a deflection could divert blood flow from direct streaming into the opposite vessel wall and control flow direction.

The material tip should be hardened to resist deformation. This may be accomplished by solvent dipping to extract plasticisors (if PVC or vinyl) or locally dipped into a harder material durometer.

The pump-outflow-cannula is placed in the patient under direct vision. Depth markings/indicators are provided on the pump-outflow-cannula body indicating placement depth into the vessel. These markings display 1-cm indicator lines (range 1-cm to 10-cm) from the most distal opening, and range from 3-cm to 10-cm for a pump-inflow-cannula.

Depth markings may be circumferential or sectors. Marking may or may not be radiopaque. These depth markers may be embedded in the cannula tip wall or be coated on the cannula wall surface. The distal-end of the cannula is of common design consideration as the pump-inflow-cannula.

Preferably, but not necessarily, the pump-inflow-cannula and/or the pump-outflow-cannula are attached to the heart by means of a sewing-ring. The sewing-ring provides a means to securely locate the cannula into the heart. The sewing-ring is attached to the apex of the left ventricle by means of direct vision with the aid of a temporary positioning handle.

The sewing-ring is configured intended to provide a mechanical means to secure the cannula to the heart by providing radial compression to the cannula while mechanically fastened to the heart tissue with sutures. The sewing-ring includes a cylindrical body sized to receive the cannula outside diameter with minimal clearance. The design is essentially a "top-hat" configuration with the top removed. The brim provides the location for securing sutures to the heart as well as the position of the felt disc for tissue interface. Included in this flange is a reinforcement member that is intended to minimize suture pull-through (bolster) as the felt material may not provide the needed structural resistance. The upper "top-hat" portion includes pre-assembled umbilical tape. This enables less manipulation by the user to satisfactorily tie-off the cannula. The umbilical tape provides a larger surface area while wrapping to resist locally cutting through the sewing-ring body and cannula wall.

Prior to implantation of the cannula, the sewing-ring is placed in proximity to the left ventricle and located so that the felt-covered fabric side is facing the heart, and the central axis lumen is directly in-line with the apex of the left ventricle.

The aid of the handle provides a feature to manipulate the sewing-ring during handling and attachment. Six or more pledgeted sutures are placed through the heart tissue at even intervals approximately 60° circumferentially apart from each other around the periphery of the heart. The suture is brought through the heart tissue approximately 1-2 cm away from the apex of the heart and the final position of the sewing-ring. The sutures are pulled through the heart muscle leading away from the pledget and towards the ventricular apex. The sutures are brought through the tissue and externalized at the point that they enter the underside of the sewing-ring. The ends of each unique pledgeted string are brought through the cuff of the sewing-ring and securely fastened.

Once positioned securely on the heart, a stab wound or punch is utilized to create access to the inner chamber of the heart. The cannula is then passed through the sewing-ring into the heart. The cannula is positioned with the most distal drainage hole contained within the heart chamber.

The umbilical tape that is pre-attached to the sewing-ring body is then wrapped about the cannula and secured with a knot to minimize cannula axial movement and blood leakage between the cannula and the sewing-ring cylinder. In addition, the sewing-ring felt disc should enable clotting of any wicked blood under the sewing-ring to again inhibit blood leakage.

Alternatively, the pump-inflow-cannula and/or the pump-outflow-cannula is positioned in a major vessel or not utilized with a sewing-ring. In such circumstances a cannula-tip-stabilizer was developed to secure the cannula using purse-string sutures.

The design of the cannula-tip-stabilizer is similar to the stabilizer-rings in that it provides a wrapping means for the suture and protects the cannula from being cut into by the suture when tightened. In addition, the cannula-tip-stabilizer enables the sutures to be positioned as close to the entry site as possible with very little compression beneath the stabilizer to affect positioning or compression/abrasion.

The invention is furthermore related to a method for connecting a blood managing system to a heart and/or to an associated vessel of a human and/or an animal blood circulation comprising the following steps:

connecting a pump-inflow-cannula to a heart and/or to an associated vessel and/or connecting a pump-outflow-cannula to a heart and/or to an associated vessel as described above;

connecting a pump-outflow-cannula to a heart and/or to an associated vessel and/or connecting a pump-inflow-cannula to a heart and/or to an associated vessel as described above.

Regarding a preferred method for connecting a blood managing system in accordance with the present invention, a blood handling system is provided, in particular a blood pump, or an oxygenator, especially an extracorporeal membrane oxygenator, or a dialysis apparatus, or another medical apparatus, for connecting the blood handling system with the distal-end of the pump-inflow-cannula and/or with the distal-end of the pump-outflow-cannula.

The invention provides also a method for performing a bypass of a human and/or of an animal organ, in particular for bypassing a heart, and/or for dialysis, and/or for an active suction- or pump-assisted autotransfusion, and/or for a cardio-pulmonary bypass surgery and/or for performing a bypass within another medical use, comprising the following steps:

providing a pump-inflow-cannula for establishing a blood conduit from a heart and/or from an associated vessel to an external blood handling system, the pump-inflow-cannula comprising a body, encompassing an essentially axially extending inflow-lumen, having a distal-end for an attachment of the inflow-lumen to the blood management system, and having a proximal-end for an introduction of blood from the heart and/or from the associated vessel into the inflow-lumen, wherein at least one projection is provided at the proximal-end to deflect a heart muscle from intruding into the inflow-lumen, and the body of the pump-inflow-cannula comprises a reinforcement-means;

and/or providing a pump-outflow-cannula for establishing a blood conduit from an external blood handling system to a heart and/or to an associated vessel, the pump-outflow-cannula comprising a body encompassing an essentially axially extending outflow-lumen having a distal-end for an introduction of blood from the blood management system into the outflow-lumen, and having a proximal-end for an attachment of the outflow-lumen to the heart and/or to the associated vessel, and the body of the pump-outflow-cannula comprises a reinforcement-means;

and/or providing a blood handling system, in particular a blood pump, or an oxygenator, especially an extracorporeal membrane oxygenator, or a dialysis apparatus, or another medical apparatus;

and/or fixing the proximal-end of the pump-inflow-cannula at the heart and/or at the associated vessel, in particular fixing the pump-inflow-cannula by a sewing technique;

and/or fixing the proximal-end of the pump-outflow-cannula at the heart and/or at the associated vessel, in particular fixing the pump-outflow-cannula by a sewing technique;

and/or the blood handling system is connected with the distal-end of the pump-inflow-cannula and/or with the distal-end of the pump-outflow-cannula.

BRIEF DESCRIPTION OF THE DRAWINGS

In the following, the invention will be explained in more detail with reference to the drawings.

FIG. 1 shows a pump-inflow-cannula with two projections;

FIG. 2b shows a reinforcement-means for a projection according to FIG. 2a;

FIG. 5 shows a sewing-ring accessory;

FIG. 7 shows a pump-outflow-cannula;

FIG. 8b is a sectional view of FIG. 8a;

DESCRIPTION OF THE PREFERRED EMBODIMENTS

Figure 2A:
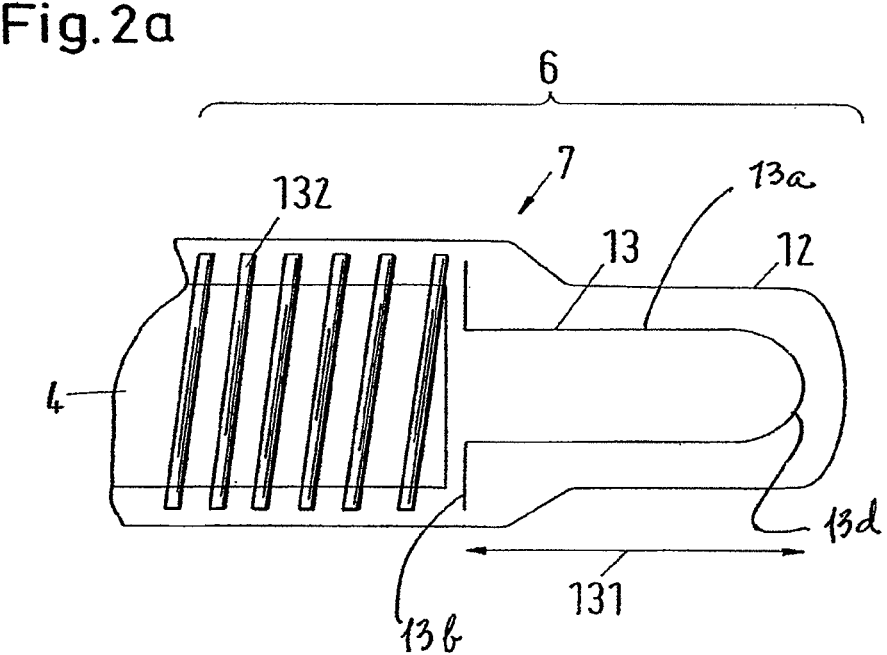
FIG. 2a shows a special embodiment of a projection.

In FIG. 1 a pump-inflow-cannula according to the present invention is schematically displayed. The pump-inflow-cannula 1 providing a blood conduit from a heart 2 and/or from an associated vessel to an external blood handling system comprises a body 3, encompassing an essentially axially extending inflow-lumen 4, having a distal-end 5 for an attachment of the inflow-lumen 4 to the blood handling system, and having a proximal-end 6 for an introduction of blood from the heart 2 and/or from the associated vessel into the inflow-lumen 4. In the present example of FIG. 1 are two projections 7 provided at the proximal-end 6 to deflect a heart muscle from intruding into the inflow-lumen 4. Preferably, the projections 7 are a continuation of the pump-inflow-cannula 1 wall thickness and not a separate component. According to the invention, the body 3 of the pump-inflow-cannula 1 comprises a reinforcement-means 8.

Since the pump-inflow-cannula 1 is placed under direct vision, it must provide the physician an indication of the proximal tip location within the heart 2. Thus, depth-indicators 18 are provided on body 3 of the pump-inflow-cannula 1 indicating placement depth from the epicardial surface of the heart 2. These depth-indicators 18 may display for example 1-cm indicator lines from 3-cm to 10-cm on the pump-inflow-cannula and from 1-cm to 10-cm on the pump-outflow-cannula. The depth-indicators 18 are circumferential or sectors and may or may not be radiopaque. In the present embodiment, the depth-indicators 18 are imbedded in the cannula wall, that is, in the body 3 of the pump-inflow-cannula 1.

To provide long-term biocompatible surfaces to the blood and tissue, the preferred cannula material is carbothane (polycarbonate-based urethane), but other urethane, PVC, vinyl materials, or other elastomeric materials may be utilized. The preferred cannula material durometer is 70-90 Shore A but can range from 50 to 100 Shore A.

The cannula body 3 is intended to provide a conduit from the blood supply to the extracorporeal device circuit located outside the body. Therefore, the body 3 of the pump-inflow-cannula 1 provides blood passage as well as structural support to the conduit. In addition, the cannula body 3 contacts both internal organs/tissues and permits external handling of the device.

The pump-inflow-cannula 1 is "tunneled" through a passage emerging out through the skin. The cannula portion 9 contained within the body and slightly emerging is reinforced by a reinforcement-means 8 to prevent collapse from tissue compression and from bending. In the example of FIG. 1 the reinforcement-means 8 is a flat spring 8 made of stainless steel (0.02" wide×0.005" thick with a pitch ranging from 0.002" to 0.040") and is totally encapsulated in a polymer, and to maintain a small profile, the spring 8 is located within a wall structure 11 of the body 3 of the pump-inflow-cannula 1.

The reinforcement should stop outside the emergence from the skin of the patient to enable cross-clamping the cannula without cannula damage. Therefore, the pump-inflow-cannula 1 of FIG. 1 includes a compressible and/or bendable system-portion 10, allowing cross-clamping of the cannula.

The cannula portion at the emergence site must affect tissue healing so as not to result in channeling about the cannula for bacteria to enter. To supplement the cannula sealing, a wrap 17 of a polyester velour material is wound and attached about the cannula. This wrap 17 provides a means to enable tissue in-growth to enter the interstitial spaces of the fabric and result in an effective seal. This tissue in-growth also provides an additional structural support to resist movement of the pump-inflow-cannula 1, skin separation during movement and pull-out of the cannula 1.

Figure 2B:
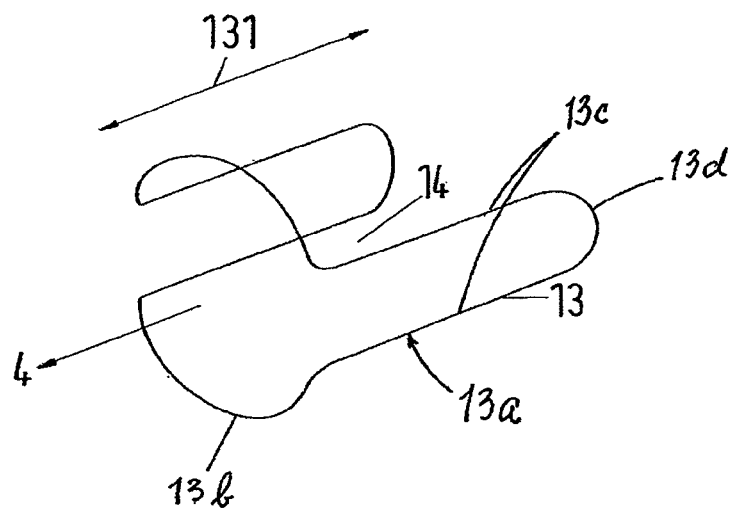

FIG. 2a shows a special embodiment of a projection 7 of a pump-inflow-cannula 1 in a sectional view. The projection 7 is spring reinforced by means of a tip-spring 13, which tip-spring 13 can be seen in more detail in FIG. 2b. By providing the tip-spring 13, the projection 7 is able to resist flapping during blood passage and/or to provide additional resistance from inward deflection of the heart muscle from intruding into the inflow-lumen 4. An axial extension of the projection 7 is between 0.25" and 0.75", preferably 0.46", and the tip-spring 13 has an arcuate spring base segment from which spring arms 13a, each with an axial extension 131 of between 0.15" and 0.70", preferably 0.40", extend. Each spring arm 13a in turn is defined by spaced-apart spring arm portions which are joined at their respective ends by a spring arm end section 13d. Spring arms 13a, and/or tip-valleys 14 between them, may be positioned 180° apart about the periphery of the inflow-lumen 4, in case that two projections 7 are provided. As shown in FIG. 2a, the tip-spring 13 is preferably encased in the projection 7 to avoid a contact of the tip-spring 13 with blood.

To reduce blood trauma, a blood exposed surface 12 of the projection 7 provided at the proximal-end 6 is rounded.

There are two projections 7 provided at the proximal-end 6 being separated by a tip-valley 14. It is understood that in another embodiment only one projection 7 may be provided or in a third embodiment more than two projections 7, for example three or four projections 7, may be provided, separated from each by a valley 14.

The fluid flow pattern created by the shape of the tip profile in the pump-inflow-cannula 1 presents unique flow characteristics compared to known cannulae with luminal access holes. Full fluid flow develops quickly in the pump-inflow-cannula 1 in accordance with the invention, leaving relatively little dead-space at low flow rates (i.e. 0.5 l/min). Over extended periods of time, very low flow areas can initiate blood clots that could release and become lodged down-stream in the pump, oxygenator or patient organs. The Computational Fluid Dynamics (CFD) analysis depicts this condition and was verified in a real pump-inflow-cannula 1 as well as in a real cannula known from the state of the art.

The tip of the proximal-end 6 of the pump-inflow-cannula 1 of FIG. 2a incorporates a radiopaque feature 132 to enable fluoroscopic imaging of the cannula tip for post-surgical placement assessment. This is accomplished by incorporating a stainless steel spring 132 within the tip. In another embodiment, the radiopaque feature 132 may be, for example, the tip-spring 13 itself. Alternatively, markers 132 made from tantalum, stainless steel, or other radiopaque materials may be utilized. The indicator 132 provides a reference feature to identify tip location within a vessel. Alternatively, the feature may surround the lumen at the proximal-end 6 of the pump-inflow-cannula 1 (i.e. cylinder) and may be embedded in the cannula tip wall or be coated on the cannula wall surface. The size of the indicator should be a minimum of 0.025" projected area.

Figure 3:
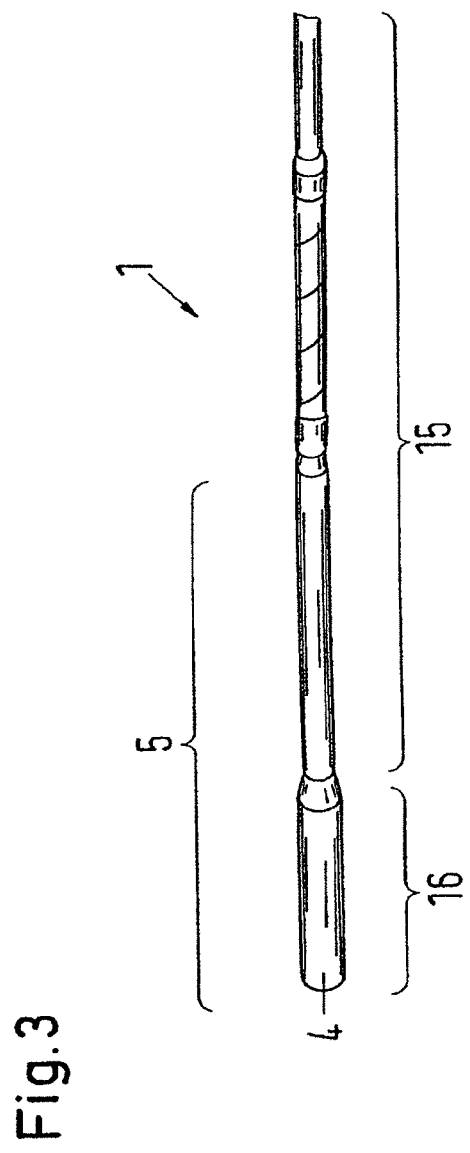
FIG. 3 shows a transition from 7.2 mm to ⅜" lumen of the distal-end of a pump-inflow-cannula.

FIG. 3 displays a special embodiment of the distal-end 5 of a pump-inflow-cannula 1, transitioning from a straight 7.2 mm lumen 15 to ⅜" lumen 16, capable of receiving a ⅜" tube connector, in particular a barbed ⅜" tube connector diameter.

The distal-end 5 of the pump-inflow-cannula 1 may have two different configurations: a straight 7.2 mm inflow-lumen 4, or a convertible cannula(e) that contains a segment 15 of 7.2 mm lumen and a transition to ⅜" lumen 16 capable of receiving a ⅜" tube barbed connector, as shown in FIG. 3.

In the convertible design of FIG. 3, the barbed fitting and associated tunneler cap can be utilized for initial cannula tunneling placement. The ⅜" barbed connector would be compatible with the ⅜" tubing set and connected to the aforementioned Levitronix CentriMag Blood Pump, which is the right choice for less than 30-day use, or to other ⅜" devices. Upon patient assessment with a short-term blood pump, the cannula would be trimmed to the 7.2 mm lumen 15 for connection e.g. to the Levitronix UltraMag Blood Pump, which is especially used for long-term support, eliminating the need to trade-out cannulae, saving a surgical intervention.

Figure 4:
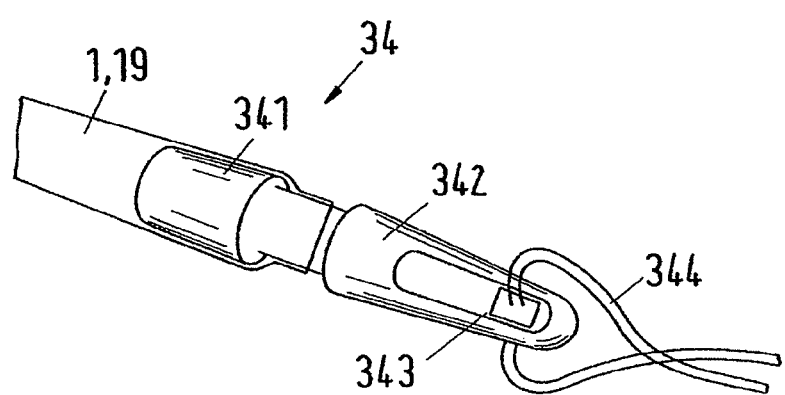
FIG. 4 shows a tunneler-plug.

In applications where the UltraMag Blood Pump is the primary pump interface, the cannula may be pre-selected to include a barbed tunneler-plug 34 fitted into the 7.2 mm lumen 15. The tunneler-plug 34 is then trimmed or removed for direct pump attachment. A respective tunneler-plug 34 is shown in FIG. 4.

To assist the pump-inflow-cannula 1 and/or a pump-outflow-cannula 19 in tunneling through a tissue of a corpus of a patient, the tunneler-plug 34 is attached to the distal-end 5, 22 into the exit lumen of the pump-inflow-cannula 1 and/or of the pump-outflow-cannula 19, respectively. The tunneler-plug 34 contains a barbed fitting 341 on one end and a smooth tapering section 342 on the other end to ease passage as it (with its assembled cannula) dilates a lumen during passage.

The tunneler-plug 34 is made of a rigid polymer or a metal (polycarbonate is preferred) and may be produced by injection molding, machining, casting or stereolithography (rapid prototyping) for short-term body contact.

The tunneler-plug 34 also contains a means 343 to secure a suture 344 or an umbilical tape 344 to create a tether for assisting in pulling the assembly through the tissue.

Upon completion of passage of the cannula 1, 19 outside the body, that is, outside of the corpus of the patient, the tunneler-plug may be disconnected or cut-off from the cannula 1,19.

In FIG. 5 a sewing-ring accessory 35 is displayed, providing a means to securely connect a cannula 1, 19, in particular a pump-inflow-cannula 1, to the heart 2 of a patient.

The sewing-ring 35 is preferably attached to the apex of the left ventricle of the patient's heart 2 by means of direct vision with the aid of a temporary positioning handle (not shown in FIG. 5). The sewing-ring 35 is configured intended to provide a mechanical means to secure the cannula 1, 19 to the heart 2 by providing radial compression to the cannula 1, 19 while mechanically fastened to the heart tissue with sutures.

The sewing-ring includes a cylindrical body 351 sized to receive the cannula outside diameter with minimal clearance. The construction of the sewing-ring 35 consists of silicone material and polyester felt. Alternatively, any hemocompatible thermoplastic or thermoset elastomer may be utilized.

The design is essentially a "top-hat" configuration with the top removed. The brim 352 provides the location for securing sutures 353 to the heart as well as position of the felt disc for tissue interface. Included in this flange is a reinforcement member 354 that is intended to minimize suture pull-through (bolster) since the felt material may not provide the needed structural resistance.

The upper "top-hat" 351 portion includes pre-assembled umbilical tape 355.

This enables less manipulation by the user to satisfactorily tie-off the cannula. The umbilical tape 355 provides a larger surface area while wrapping to resist locally cutting through the sewing-ring body and cannula wall.

Prior to implantation of e.g. the pump-inflow-cannula, the sewing-ring 35 is placed for example in proximity to the left ventricle and located such that the felt-covered fabric side is facing the heart 2, and the central axis lumen is directly in-line with the apex of the left ventricle.

Figure 6A:
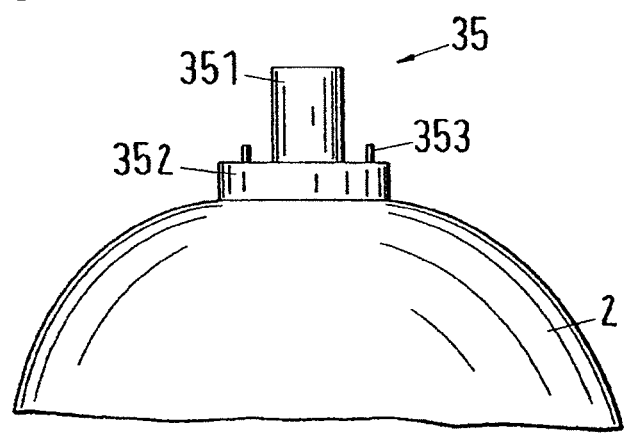
FIG. 6a shows a sewing-ring in accordance with FIG. 5 attached to a heart.
Figure 6B:
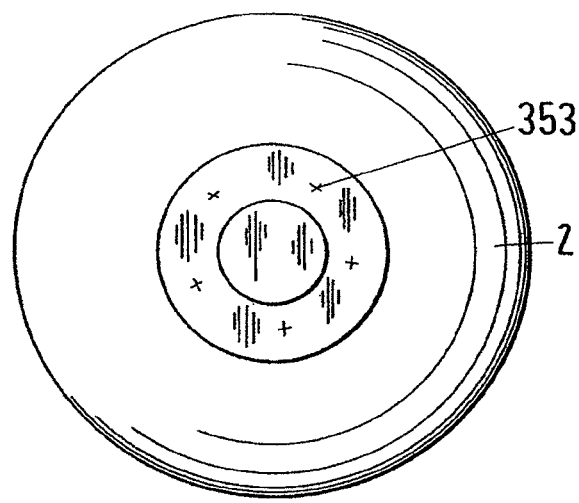
FIG. 6b is a bottom view of FIG. 6b.

The aid of the aforementioned handle provides a feature to manipulate the sewing-ring 35 during handling and attachment. As displayed in FIG. 6a and FIG. 6b, six or more pledgeted sutures 353 are placed through the heart tissue at even intervals approximately 60° circumferentially apart from each other around the periphery of the heart 2. The suture 353 is brought through the heart tissue approximately 1-2 cm away from the apex of the heart 2 and the final position of the sewing-ring. The sutures 353 are pulled through the heart muscle leading away from the pledget and towards the ventricular apex. The sutures 353 are brought through the tissue and externalized at the point that they enter the underside of the sewing-ring 35. The ends of each unique pledgeted string are brought through the cuff of the sewing-ring 354 and securely fastened.

Once positioned securely on the heart 2, a stab wound or punch is utilized to create access to the inner chamber of the heart 2. The cannula 1, 19 is then passed through the sewing-ring 35 into the heart 2. The cannula 1, 19 is positioned with the most distal drainage hole contained within the heart chamber.

The umbilical tape 355 that is pre-attached to the sewing-ring body is then wrapped about the cannula 1, 19 and secured with a knot to minimize cannula axial movement and blood leakage between the cannula 1, 19 and the sewing-ring cylinder. In addition, the sewing-ring felt disc should enable clotting of any wicked blood under the sewing-ring 35 to again inhibit blood leakage.

FIG. 7 shows a special embodiment of a pump-outflow-cannula 19 in accordance with the present invention.

The pump-outflow-cannula 19 of FIG. 7, providing a blood conduit from an external blood handling system to a heart 2 and/or to an associated vessel, comprises a body 20 encompassing an essentially axially extending outflow-lumen 21, having a distal-end 22 for an introduction of blood from the blood management system into the outflow-lumen 21, and having a proximal-end 23 for an attachment of the outflow-lumen 21 to the heart 2 and/or to the associated vessel. According to the invention, the body 20 of the pump-outflow-cannula 19 comprises a reinforcement-means 24.

Thereby, the pump-outflow-cannula 19 displayed in FIG. 7, comprises a reinforced body-portion 25 to be essentially contained within a corpus of a human or an animal, especially to be contained within the corpus and extending beyond a skin of the corpus, and further comprising a compressible and/or bendable system-portion 26 to be located outside of the corpus.

In the present example, the reinforcement-means 24 are located within a wall structure 27 of the body 20 of the pump-outflow-cannula 19 and the reinforcement-means 24 is a wire 24, in particular a wire 24 made of plastic, and/or made of a composite material, and/or made of a metal, especially made of a stainless steel.

As shown in FIG. 7, the reinforcement-means 24 is preferably a helical flat spring 24.

The pump-outflow-cannula 19 includes at the proximal-end 23 a securing-means 30 for securing the proximal-end 23 to the heart 2 and/or to the associated vessel, and includes in the example of FIG. 7 a vascular graft 30 and may comprise an embedded winding 30 for securing a vascular graft 30.

The design shown in FIG. 7 incorporates a standard vascular graft 30 (i.e. diameter 8 mm) and suturing technique to the vessel wall so as to create a side opening in the vessel for blood passage. The proximal-end 23 of the pump-outflow-cannula 19 is configured so as to enable positioning the cannula proximal-end 23 into the body of the graft 30 through the lumen. A suture is then wrapped about the graft 30 to secure the cannula 19 within it and provide a leak-tight joint.

The proximal-end 23 of the pump-outflow-cannula 19 may be placed within the lumen of a vascular graft 30 (8 mm graft) attached to the aortic artery. The graft 30 is intended to prevent accidental decannulation and to reduce pressure necrosis of the vessel wall by providing a "soft" interface, and a smooth cannula-to-vessel transition. Placement of the cannula 19 within the graft 30 and not extending the pump-outflow-cannula 19 into the aorta reduces dislodgement of embolic material from the return blood flow stream. The proximal lumen of the pump-outflow-cannula 19 is a through lumen. The periphery about the tip should be 0.315", ranging from 0.100" to 0.600".

The proximal-end of the pump-outflow-cannula 19 is configured as a squared-off open lumen from the cannula body. The proximal tip is tapered on the inside diameter and straight walled on the outside diameter to minimize "dead space" about the cannula positioned within the lumen of the graft 30.

The proximal outflow cannula diameter is sized to enable maximum blood flow and fit within the vascular graft 30. To accomplish this, the cannula 19 is reinforced with flat wire 24, thereby having a minimal wall thickness. In such a design, the reinforcing wire 24 provides resistance from occlusion when the suture is wrapped about the graft 30 for securing the graft 30 to the cannula 19.

Figure 8A:
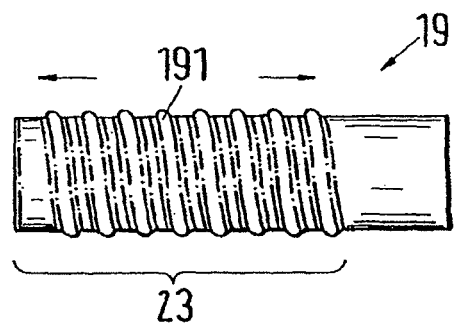
FIG. 8a shows a thread configuration at the promixal-end of a pump-outflow-cannula.
Figure 8B:

FIG. 8*a* shows a thread configuration at the promixal-end 23 of a pump-outflow-cannula 19, and FIG. 8*b* shows a sectional view of FIG. 8*a*.

The proximal-end 23 of the pump-outflow-cannula 19 is configured to enable vascular graft 30 attachment. A spiral wound vascular graft was selected (but not necessary) with the intent to screw-thread the graft on top of the cannula proximal-end 23.

Figure 8C:
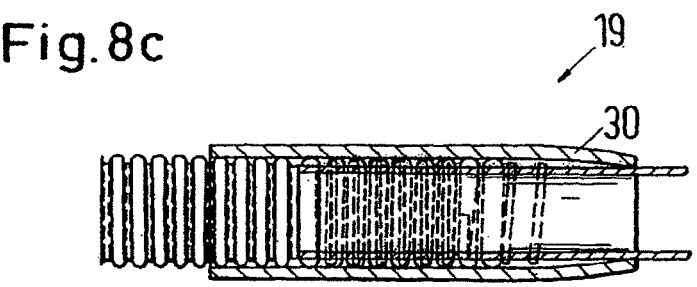
FIG. 8c shows a thread configuration according to FIG. 8a with a graft attached thereto.
Figure 8D:
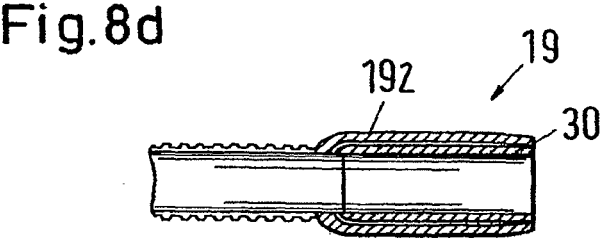
FIG. 8d shows an embodiment according to FIG. 8c with a sleeve.

A round extrusion is produced from carbothane (or the same material as the cannula), wound into a thread pitch 191 and assembled to the proximal-end 23 of the pump-outflow-cannula 19. This winding 191 is embedded in the cannula wall so as to produce a thread on the exterior of the cannula. As shown in FIG. 8*c*, the vascular graft 30 is threaded over this embedded winding 191 for attachment. According to FIG. 8*d*, a short shrink tube 192 or elastic sleeve 192 (slightly smaller than the cannula outside diameter) is fitted over the assembly to mechanically lock the graft 30 into place onto the cannula. This sleeve 192 may be bonded to the cannula body as well.

Figure 9:
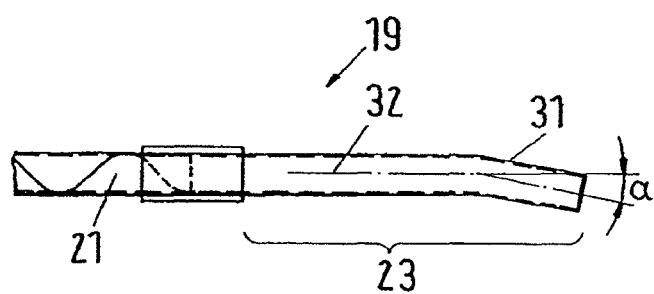
FIG. 9 shows a pump-outflow-cannula incorporating no vascular graft.
Figure 10:
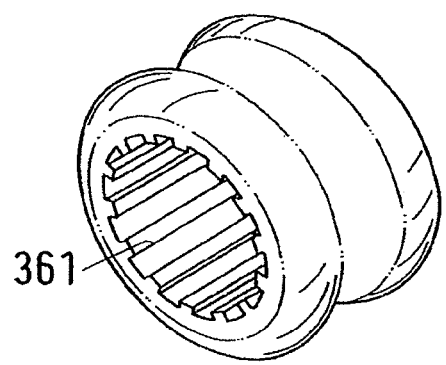
FIG. 10 shows a stabilizer-ring.

The embodiment according to FIG. 9 incorporates no vascular graft but rather positions the cannula proximal tip directly through the vessel wall. This cannula 19 is purse-string secured to the vessel wall.

The proximal-end 23 of this cannula 19 may be straight or bend by an angle □5° to 30° from an longitudinal axis 32 to create a fluid-deflection 31 at the outlet. Such a deflection 31 could divert blood flow from direct streaming into the opposite vessel wall and control flow direction.

The material tip should be hardened to resist deformation. This may be accomplished by solvent dipping to extract plasticisors (if PVC or vinyl) or locally dipped into a harder material durometer.

The pump-inflow-cannula 1 and/or the pump-outflow-cannula 19 may contain a number of securing grommets 361 slideable along the cannula length for the surgeon to suture strain-relief at strategic locations along the implant.

To enable the cannula 1, 19 to be secured with sutures without resulting in the occlusion of the cannula lumen a stabilizing-ring 36 can be provided. The securing grommets 361 are designed to fit about the outside diameter of the cannula 1, 19. Its shape provides a means for wrapping a suture while providing a feature to keep the suture from inadvertently sliding off. The grommet 361 may be made from silicone, polyurethane, TPR rubber, or other elastomeric material compatible for long-term implant. The grommet 361 may be injection molded, cast or formed. The stabilizer-ring 36 may also be filled with a radiopaque material so that it is visible via x-ray or fluoroscopic inspection. The number of grommets 361 utilized are at the discretion of the physician to hold the internal cannula shape.

Alternative embodiments are additionally possible. Co-axial transseptal percutaneous cannula is known from the state of the art (CardiacAssist Inc., Pittsburgh, Pa.—TandemHeart Percutaneous Transseptal Ventricular Assist (PTVA) System), requiring a single vascular puncture. Such cannulae may be placed through a major vessel (internal jugular vein, external jugular vein, inferior vena cava) to access the heart.

These pump-outflow-cannula proximal-ends reside in the right atrium and the pump-inflow-cannula proximal-end resides in the left atrium—piercing through the septum.

The cannulae may be scaled up or down depending upon the desired blood flow rate and pressure drop required across the system. As such, connector fittings and tubing sizes may be compatibly substituted.

The cannula may be multi-lumen, providing a means for passage of secondary devices utilized for diagnostics or therapeutic applications. A second or third lumen may be utilized for features such as temperature sensing, blood gas sensing, pressure measurements, guidewire passage, catheter passage, flushing, vascular injections, etc. Cannulae may be treated or lined with clot-resistant coatings.

It is understood that the invention is not only related to the special embodiments discussed above, but further embodiments are also included. In particular, the invention relates to all advantageous combinations of the discussed embodiments.

What is claimed is:

1. A cannula assembly, comprising:
a blood flow cannula defining a lumen therein and comprising a first end portion configured to fluidly connect a first portion of the lumen to an external blood handling system, a reinforced body portion, and a second end portion configured to fluidly connect a second portion of the lumen to a circulatory system of a patient; and
a tunneler plug including a male fitting at a first end of the tunneler plug and a smooth tapering section at a second end of the tunneler plug; the male fitting being configured to be inserted into the first portion of the lumen to attach the tunneler plug to the first end portion of the blood flow cannula; the tunneler plug being configured and dimensioned to be pulled through a skin of the patient to pull the first end portion through the skin from within the patient to position the first end portion outside of the patient, to position the reinforced body portion to interface with the skin, and so that the second end portion is positioned within the patient;
wherein the reinforced body portion is configured to prevent collapse of the lumen from transverse compression of the reinforced body portion induced by the skin and from bending of the reinforced body portion so as to maintain fluid communication between the first portion of the lumen and the second portion of the lumen.

2. The cannula assembly of claim 1, further comprising a wrap attached to an outside surface of the reinforced body portion and configured for tissue in-growth to provide sealing between the blood flow cannula and the skin of the patient at a location where the blood flow cannula emerges from the patient.

3. The cannula assembly of claim 1, further comprising a reinforcing member within the reinforced body portion.

4. The cannula assembly of claim 3, wherein the reinforcing member comprises a spring.

5. The cannula assembly of claim 4, wherein the spring is a helical flat spring.

6. The cannula assembly of claim 1, wherein:
the second end portion is configured to extend through a wall of a heart of the patient into a ventricle of the heart to fluidly connect the second portion of the lumen with the ventricle; and
the second end portion includes one or more projections configured to extend into the ventricle to prevent heart muscle from blocking blood flow into the second portion of the lumen.

7. The cannula assembly of claim 1, wherein the male fitting comprises a barbed fitting configured to be inserted into the lumen in the first end portion of the blood flow cannula.

8. The cannula assembly of claim 1, wherein the tapering section is configured to dilate an aperture in the skin during passage through the skin.

9. The cannula assembly of claim 1, wherein the tapering section comprises an aperture configured for a suture or umbilical tape to be secured thereto, such that the suture or tape serves as a tether to assist in pulling the tunneler plug through the skin.

10. The cannula assembly of claim 1, further comprising a sewing ring comprising a flange with a first surface configured to be secured to an additional section of tissue, and a hollow projection extending from a second surface of the flange, the hollow projection being configured to receive the blood flow cannula and to secure the blood flow cannula therein.

11. The cannula of assembly claim 10, wherein the sewing ring further comprises a soft absorbent pad on the first surface thereof.

12. The cannula assembly of claim 10, wherein the sewing ring further comprises a length of tape attached thereto, configured to be tied around the blood flow cannula to secure the blood flow cannula to the sewing ring.

13. The cannula assembly of claim 1, wherein the second portion is configured to interface with a heart, an aorta, or an additional artery of the patient to fluidly connect the second portion of the lumen with the heart, the aorta, or the additional artery of the patient.

14. The cannula assembly of claim 1, wherein the second portion includes helical screw threads formed via a helical member defining a thread pitch, the reinforced body portion comprising a polymer and having the helical member embedded within the polymer so as that the helical screw threads are formed in an external surface of the polymer.

15. The cannula assembly of claim 1, wherein:
the reinforced body portion comprises a reinforcement that does not extend into the first end portion, and
the first end portion is configured to be cross-clamped without damaging the cannula.

16. A blood management system, comprising:
a blood handling system;
an inflow cannula configured to provide fluid communication between a circulatory system of a patient and an input of the blood handling system; and
an outflow cannula assembly comprising:
an outflow cannula configured to provide fluid communication between the circulatory system and an output of the blood handling system, the outflow cannula defining a lumen therein and comprising a first end portion configured to fluidly connect a first portion of the lumen to the blood handling system, a reinforced body portion, and a second end portion configured to fluidly connect a second portion of the lumen to the circulatory system; and
a tunneler plug including a male fitting at a first end of the tunneler plug and a smooth tapering section at a second end of the tunneler plug; the male fitting being configured to be inserted into the first portion of the lumen to attach the tunneler plug to the first end portion of the outflow cannula; the tunneler plug being configured and dimensioned to be pulled through a skin of the patient to pull the first end portion through the skin from within the patient to position the first end portion outside of the patient, to position the reinforced body portion to interface with the skin, and so that the second end portion is positioned within the patient;
wherein the reinforced body portion is configured to prevent collapse of the lumen from transverse compression of the reinforced body portion induced by the skin and from bending of the reinforced body portion so as to maintain fluid communication between the first portion of the lumen and the second portion of the lumen.

17. The system of claim 16, further comprising a sewing ring comprising a flange with a first surface configured to be secured to an additional section of tissue, and a hollow projection extending from a second surface of the flange, the hollow projection being configured to receive the inflow or outflow cannula and to secure the inflow or outflow cannula therein.

18. The system of claim 16, wherein the second end portion includes helical screw threads configured to be rotationally threaded into a vascular graft fluidly connected to the circulatory system of the patient, the helical screw threads being formed via a helical member defining a thread pitch, the reinforced body portion comprising a polymer and having the helical member embedded within the polymer so as that the helical screw threads are formed in an external surface of the polymer.

19. The system of claim 16, wherein:
the reinforced body portion comprises a reinforcement that does not extend into the first end portion, and
the first end portion is configured to be cross-clamped without damaging the cannula.

20. A cannula assembly, comprising:
a blood flow cannula defining a lumen therein and comprising a first end portion configured to fluidly connect a first portion of the lumen to a blood handling system, a reinforced body portion, and a second end portion configured to fluidly connect a second portion of the lumen to a circulatory system of a patient;
a tunneler plug including a male fitting at a first end of the tunneler plug and a smooth tapering section at a second end of the tunneler plug; the male fitting being configured to be inserted into the first portion of the lumen to attach the tunneler plug to the first end portion of the blood flow cannula; the tunneler plug being configured and dimensioned to be pulled through a skin of the patient to pull the first end portion through the skin from within the patient to position the first end portion outside of the patient, to position the reinforced body portion to interface with the skin, and so that the second end portion is positioned within the patient; and
at least two spaced-apart projections extending from the second end portion of the blood flow cannula and configured to prevent blocking of the second portion of the lumen via tissue of the patient,
wherein the reinforced body portion is configured to prevent collapse of the lumen from transverse compression reinforced body portion induced by the skin and from bending of the reinforced body portion so as to maintain fluid communication between the first portion of the lumen and the second portion of the lumen.

* * * * *